US010173212B2

(12) United States Patent
Jung et al.

(10) Patent No.: US 10,173,212 B2
(45) Date of Patent: Jan. 8, 2019

(54) METHOD FOR REGENERATING HYDROGENATION CATALYST FOR PHTHALATE COMPOUND

(71) Applicant: HANWHA CHEMICAL CORPORATION, Seoul (KR)

(72) Inventors: Ki Taeg Jung, Daejeon (KR); Kyong Jun Yoon, Daejeon (KR); Hyo Suk Kim, Daejeon (KR); Jang Young Kwak, Daejeon (KR); Pil Je Seong, Daejeon (KR); Kyoung Il Lee, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 0 days.

(21) Appl. No.: 15/544,294

(22) PCT Filed: Mar. 31, 2016

(86) PCT No.: PCT/KR2016/003341
§ 371 (c)(1),
(2) Date: Jul. 18, 2017

(87) PCT Pub. No.: WO2016/159691
PCT Pub. Date: Oct. 6, 2016

(65) Prior Publication Data
US 2018/0015450 A1    Jan. 18, 2018

(30) Foreign Application Priority Data
Apr. 1, 2015   (KR) .......................... 10-2015-0046225

(51) Int. Cl.
| | | |
|---|---|---|
| *B01J 23/96* | (2006.01) | |
| *B01J 38/52* | (2006.01) | |
| *C07C 67/283* | (2006.01) | |
| *B01J 37/06* | (2006.01) | |
| *B01J 23/46* | (2006.01) | |

(52) U.S. Cl.
CPC ............. *B01J 38/52* (2013.01); *B01J 23/96* (2013.01); *C07C 67/283* (2013.01); *B01J 23/462* (2013.01); *B01J 37/06* (2013.01)

(58) Field of Classification Search
CPC .......... B01J 23/96; B01J 38/52; C07C 67/283
See application file for complete search history.

(56) References Cited

U.S. PATENT DOCUMENTS

| | | | |
|---|---|---|---|
| 4,322,315 A | 3/1982 | Drake | |
| 4,331,557 A | 5/1982 | Drake | |
| 5,286,898 A * | 2/1994 | Gustafson | ............. C07C 67/303 |
| | | | 560/127 |
| 6,803,341 B2 * | 10/2004 | Lo | .......................... B01J 23/462 |
| | | | 502/332 |
| 2002/0019559 A1 * | 2/2002 | Brunner | .................. C07C 51/36 |
| | | | 560/55 |
| 2012/0296111 A1 * | 11/2012 | Konigsmann | ............ B01J 21/08 |
| | | | 560/127 |

FOREIGN PATENT DOCUMENTS

| | | |
|---|---|---|
| CN | 102219689 | * 10/2011 |
| CN | 101254475 | 4/2012 |
| CN | 103816923 | * 5/2014 |
| JP | 44-017741 | 8/1969 |
| JP | 51-074997 | 6/1976 |
| JP | 05-279282 | 10/1993 |
| JP | 07-178341 | 7/1995 |
| JP | 09-117665 | 5/1997 |
| JP | 09-215934 | 8/1997 |
| JP | 3629952 | * 3/2005 |
| JP | 3726504 | 12/2005 |
| JP | 5044649 | 10/2012 |
| JP | 2013-513477 | 4/2013 |
| KR | 10-1999-0067193 | 8/1999 |
| KR | 10-2007-0015458 | 2/2007 |
| KR | 10-2009-0037902 | 4/2009 |
| KR | 10-2009-0037903 | 4/2009 |
| WO | 2014-014466 | 1/2014 |
| WO | 2014-203601 | 12/2014 |

OTHER PUBLICATIONS

Argyle et al., "Heterogeneous Catalyst Deactivation and Regeneration: A Review," Catalysts 2015, 5, 145-269.*
English Translation of CN102219689, Oct. 19, 2011, pp. 1-6.*
English Translation of CN103816923, May 28, 2014, pp. 1-12.*
English Translation of JP3629952, Mar. 16, 2005, pp. 1-9.*
Search Report & Written Opinion, Patent Cooperation Treaty, dated Jun. 27, 2016, Application No. PCT/KR2016/003341.
Chung, Young-Min, et al., "Methods for the Regeneration of Titanium-containing Molecular Sieve Catalysts" Theories and Applications of Chem. Eng., 2005, vol. 11, No. 2 pp. 2614-2617.

* cited by examiner

*Primary Examiner* — Pancham Bakshi
*Assistant Examiner* — Mark R Luderer
(74) *Attorney, Agent, or Firm* — Lex IP Meister, PLLC

(57) ABSTRACT

The present invention relates to a method for regenerating a hydrogenation catalyst for a phthalate compound. More specifically, the present invention regenerates a hydrogenation catalyst for a phthalate compound by using an alcohol, and thereby provides a method for regenerating a hydrogenation catalyst for a phthalate compound that is capable of continuously hydrogenating a phthalate compound without replacing a catalyst in a catalytic reactor, and is also capable of improving operational stability and the lifetime of a catalyst and increasing economic efficiency.

9 Claims, No Drawings

METHOD FOR REGENERATING HYDROGENATION CATALYST FOR PHTHALATE COMPOUND

TECHNICAL FIELD

The present invention relates to a method for regenerating a hydrogenation catalyst for a phthalate compound, more specifically, to a method for regenerating a hydrogenation catalyst for a phthalate compound, capable of regenerating the catalyst used during hydrogenation by using an alcohol and thus reusing the same in a hydrogenation reaction after a hydrogenation reaction of a phthalate compound.

BACKGROUND ART

In general, phthalate compounds can be obtained by an esterification reaction of an acid, such as phthalic acid, terephthalic acid, isophthalic acid, or an anhydride thereof, with an alcohol. In order to neutralize catalysts used in the esterification reaction and remaining acid components after the esterification reaction, basic compounds such as sodium carbonate ($Na_2CO_3$), sodium hydroxide (NaOH), calcium carbonate ($CaCO_3$) and potassium hydroxide (KOH) are used. Accordingly, impurities such as metal ions including $Na^+$, $K^+$, $Ca^{2+}$ liberated from such basic compounds, metal salt compounds produced by binding with the metal ions, or other reaction by-products may remain in a trace amount in the phthalate compounds.

When a trace amount of these metal ions or metal salt compounds is contained in the phthalate compounds, there is no significant influence on the quality of the phthalate compounds themselves, but they can act as a catalyst poison to the hydrogenation catalyst used in the hydrogenation reaction of the phthalate compounds, thereby becoming one of the main causes for lowering activity of the catalyst. More specifically, the metal ions or metal salt compounds exist in a state of not being sufficiently dissolved or dispersed and can be readily adsorbed to the hydrogenation catalyst physically or chemically, and thus the activity of the catalyst is drastically lowered.

Further, during the hydrogenation reaction of the phthalate compounds (that is, a hydrogen addition reaction), the activity of the catalyst is continuously lowered. When the activity of the catalyst is lowered to a certain level, catalyst replacement is required. In this case, with frequent catalyst replacements, economic efficiency may be reduced due to a decrease in production along with an increase in the cost of operation and replacement.

Accordingly, there is a need for a method for regenerating a hydrogenation catalyst that acts as a catalyst poison after the hydrogenation reaction of a phthalate compound. In addition, there is a need for a method capable of solving the problem of cost increase and production decrease caused by catalyst replacement during the hydrogenation addition reaction.

DETAILED DESCRIPTION OF THE INVENTION

Technical Problem

It is an object of the present invention to provide a method for regenerating a hydrogenation catalyst for a phthalate compound, capable of regenerating activity of the catalyst in a reactor through supply of alcohol without recovering the catalyst in the reactor during the hydrogenation reaction of the phthalate compound, thereby prolonging the lifetime of the catalyst by restoring the performance of the catalyst, and thereby improving the process operation cost, the operational stability, and the economic efficiency of the process.

Technical Solution

The present invention provides a method for regenerating a hydrogenation catalyst for a phthalate compound, comprising the step of performing a hydrogenation reaction of a phthalate compound including reacting a phthalate compound with hydrogen in the presence of a hydrogenation catalyst, and then regenerating the hydrogenation catalyst at a temperature of 80° C. or more using an alcohol.

The alcohol may be at least one selected from the group consisting of octanol, hexanol, butanol, propanol, ethanol, 2-ethylhexanol, and an alcohol having an isomer structure of the alcohols. It may also include an alcohol of an isomer of the above-mentioned alcohols.

It is preferable that the step of regenerating the hydrogenation catalyst is performed at a temperature of 80 to 300° C. by using an alcohol such that the Reynolds number of the alcohol passing through a catalyst layer is 2100 or more. The regenerating step, for example, can be performed for about 50 minutes to 6 hours. However, since the regeneration time may vary depending on the amount of the catalyst used in the reaction, the degree of lowering of catalytic activity, the flow rate of the alcohol during regeneration, or the like, the regeneration time is not limited thereto.

In addition, the present invention includes a step of continuously reusing the regenerated catalyst in the hydrogenation reaction of a phthalate compound after the step of regenerating the hydrogenation catalyst.

Moreover, the hydrogenation catalyst includes at least one selected from the group consisting of ruthenium (Ru), palladium (Pd), rhodium (Rh), platinum (Pt) and nickel (Ni).

The phthalate compound is at least one selected from the group consisting of phthalate, terephthalate, isophthalate, and a carboxylic acid compound thereof.

The phthalate compound may include a metal ion or a metal salt compound as an impurity. The purity of the phthalate compound may be 98% or higher. The phthalate compound may be dioctyl terephthalate (DOTP).

The hydrogenation reaction of the phthalate compound may be performed by additionally using an alcohol having 2 or more carbon atoms.

Advantageous Effects

According to the present invention, the hydrogenation catalyst in which a decomposition reaction has occurred by hydrogen is washed for a predetermined period of time with a high-temperature alcohol, such that a method for regenerating a catalyst capable of improving the lifetime thereof by recovering the performance of the catalyst is provided.

Accordingly, when preparing a hydrogenation reaction product by the hydrogenation reaction using a catalytic reactor, since the present invention regenerates the catalyst for the hydrogenation reaction, it is possible to reduce the repeated replacement of the catalyst and the repeated interruption of the operation, thereby increasing not only the stability of the operation but also the economic efficiency of the process by improving the lifetime of the catalyst. In particular, the present invention not only reduces the amount of use of a catalyst required in the reactor and prolongs the replacement cycle, but can also allow reuse of the alcohol used in the regeneration without separation/purification thereof in the reaction, thereby improving the operational stability of the process and the economic efficiency in a commercial scale process.

DETAILED DESCRIPTION OF THE EMBODIMENTS

A variety of modifications may be made to the present invention and there are various embodiments of the invention, examples of which will now be described in detail. However, it is not intended to limit the present invention to particular embodiments, and it is to be appreciated that all modifications, equivalents, and substitutions that do not depart from the spirit and technical scope of the invention are encompassed in the present invention. In addition, in the description of the present disclosure, the detailed descriptions of known related techniques thereof may be omitted if they make the gist of the present invention unclear.

In the present invention, it will be understood that the terms first, second, etc. may be used to describe various elements, and these terms are only used to distinguish one element from another element. For instance, a first element could be termed a second element without departing from the teachings of the present invention. Similarly, the second element could be termed the first element.

As used herein, the singular forms "a," "an," and "the" may be intended to include the plural forms as well, unless the context clearly indicates otherwise. In the present disclosure, it will be further understood that the terms "comprise", "include", "have", etc. specify the presence of stated features, integers, steps, operations, elements, components, and/or combinations thereof, but do not preclude the presence or addition of one or more other features, integers, steps, operations, elements, components, and/or combinations thereof.

According to a preferable embodiment of the present invention, a method for regenerating a hydrogenation catalyst for a phthalate compound, comprising the steps of performing a hydrogenation reaction of a phthalate compound including reacting a phthalate compound with hydrogen in the presence of a hydrogenation catalyst, and then regenerating the hydrogenation catalyst at a temperature of 80° C. or more using an alcohol, is provided.

The present invention relates to a method for regenerating a hydrogenation catalyst used in a hydrogenation reaction. More specifically, the present invention relates to a method for regenerating a catalyst after a hydrogenation reaction of a phthalate compound, which not only regenerates the activity of the used catalyst, but also has economic effects such as an increase in the product yield as well as reduction of costs, by regenerating the catalyst in a reactor without performing a replacement operation.

Accordingly, the present invention can allow direct reuse of the hydrogenation catalyst of which activity has been continuously regenerated without catalyst replacement, in the hydrogenation reaction. Further, the alcohols used for the regeneration of the hydrogenation catalyst can also be reused in the reaction without separation/purification.

Specifically, as the reaction proceeds during the hydrogenation reaction after the hydrogenation reaction of the phthalate compound, the activity of the catalyst is lowered by adsorption or the like on the surface of the catalyst. Accordingly, the present invention is characterized by providing a method of regenerating the activity of the catalyst by removing impurities in the catalyst and of pore clogging, etc., using an alcohol after the completion of the hydrogenation reaction.

Hereinafter, the method for regenerating a hydrogenation catalyst for a phthalate compound according to the preferable embodiment of the present invention will be described.

The present invention includes a method for hydrogenating a phthalate compound which is performed before regenerating a hydrogenation catalyst. Such a hydrogenation method of the present invention includes a step of reacting a phthalate compound with hydrogen in the presence of a hydrogenation catalyst. The hydrogenation reaction of the phthalate compound may be carried out by additionally using an alcohol having 2 or more carbon atoms.

The present invention provides a method for regenerating a hydrogenation catalyst including a step of regenerating the catalyst used in the hydrogenation reaction at a temperature of 80° C. or more using an alcohol.

As described above, in the hydrogenation reaction process using the hydrogenation catalyst, the main causes of a decrease in the activity of the catalyst are salts present in the raw materials and heavy materials generated during the reaction, and they become a poison in the catalyst, thereby deteriorating the performance of the catalyst. When the performance of the catalyst is deteriorated, the conversion rate of the reaction decreases, and the catalyst needs to be replaced.

In addition, the materials poisoning the catalyst during the reaction have a high boiling point or are poorly soluble in phthalate and terephthalate compounds.

Accordingly, in the case in which the performance of the catalyst is deteriorated, a method of regenerating a catalyst through an alcohol and a mixture including the alcohol, without replacing the catalyst, is provided.

In particular, the present invention can easily remove the materials poisoning the catalyst through a high-temperature alcohol, thereby readily regenerating the activity of the hydrogenation catalyst.

In the present invention, the alcohols used for the regeneration of the hydrogenation catalyst may be alcohols having 2 or more carbon atoms, and they can be introduced into a catalytic reactor at a temperature of 80° C. or more. Preferably, the alcohol may be at least one selected from the group consisting of octanol, hexanol, butanol, propanol, ethanol, 2-ethylhexanol, and an alcohol having an isomer structure of the alcohols.

In particular, in the present invention, it is preferable to confirm that the catalytic activity is lowered after the completion of the hydrogenation catalytic reaction and to perform the regeneration of the catalyst at a temperature of 80° C. or more while supplying the alcohols to the catalytic reactor. Further, in the present invention, when the alcohol is used in the catalyst regeneration, it is more preferable to perform the catalyst regeneration for a predetermined period of time and at a temperature of 80° C. or more.

That is, in order to remove the poisoning materials in the catalyst, the alcohols are supplied at 80° C. or more, preferably at 80 to 300° C., and more preferably at 120 to 200° C. However, the range thereof is not particularly limited as long as the temperature of supply is 80° C. or more.

The flow rate of the alcohol used in the catalyst regeneration is preferably selected so that the Reynolds number ($N_{Re}$) of the alcohol passing through the catalyst layer is 2100 or more, and more preferably 4000 or more, but is not limited thereto. When the Reynolds number ($N_{Re}$) is in the range of 4000 or more, the flow rate of the alcohol falls within the turbulent flow range. If turbulence occurs at this time, it is more effective for the catalyst regeneration in accordance with the flow characteristics of the alcohol. The Reynolds number is a number that determines the flow pattern of a fluid (laminar flow and turbulent flow), as is well known in the art.

Therefore, according to the preferable one embodiment of the present invention, it may be preferable to perform the step of regenerating the hydrogenation catalyst at a temperature of 80 to 300° C. using the alcohol such that the Reynolds number of the alcohol passing through the catalyst layer is 2100 or more.

In addition, the step of regenerating the hydrogenation catalyst may be performed at a temperature of 80 to 300° C. for 50 minutes to 6 hours using the alcohol. However, since the regeneration time may vary depending on the amount of the catalyst used in the reaction, the degree of lowering of the catalyst activity, the flow rate of the alcohol during regeneration, and the like, the regeneration time is not limited thereto.

The present invention includes a step of continuously reusing the regenerated catalyst in the hydrogenation reaction of the phthalate compound after the step of regenerating the hydrogenation catalyst.

Accordingly, since the regenerated catalyst can be used again in the hydrogenation reaction of the phthalate compound in accordance with the supply of the alcohol having 2 or more carbon atoms and hydrogen while remaining intact in the reactor, the hydrogenation reaction can be carried out in an economical manner.

In other words, the present invention can regenerate the activity of the catalyst and can reuse the regenerated catalyst in the hydrogenation reaction by introducing a high-temperature alcohol into the catalytic reactor to perform a washing process. The present invention can therefore carry out the hydrogenation reaction again without replacing the catalyst, thereby improving the operability of the process and economic efficiency. In addition, the alcohols used for the regeneration of the catalyst can be reused without separation and purification.

Herein, the regenerated hydrogenation catalyst may include at least one selected from the group consisting of ruthenium (Ru), palladium (Pd), rhodium (Rh), platinum (Pt), and nickel (Ni).

Meanwhile, the hydrogenation reaction of the phthalate compound will now be described in detail.

The reaction object of the hydrogenation process of the present invention is a phthalate compound, and the process is a reaction in which hydrogen is added to a benzene ring of the phthalate compound by hydrogenation to be converted into a corresponding cyclohexane dicarboxylate compound.

The phthalate compound may be at least one selected from the group consisting of phthalate, terephthalate, isophthalate, and a corresponding carboxylic acid compound thereof.

The phthalate compound may be represented by Chemical Formula 1 below.

[Chemical Formula 1]

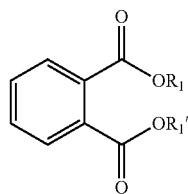

In Chemical Formula 1, $R_1$ and $R_1'$ may independently be the same or different, and may be hydrogen, or a straight or branched chain alkyl group having 1 to 20 carbon atoms, preferably 4 to 20 carbon atoms, more preferably 5 to 20 carbon atoms, and even more preferably 5 to 10 carbon atoms.

Specific examples of the phthalate compound include dibutyl phthalate (DBP), dihexyl phthalate (DHP), dioctyl phthalate (DOP), di-n-octyl phthalate (DnOP), diisononyl phthalate, diisodecyl phthalate (DIDP), etc., but are not limited thereto. These compounds can be used alone or in combination of two or more.

The terephthalate compound may be represented by Chemical Formula 2 below.

[Chemical Formula 2]

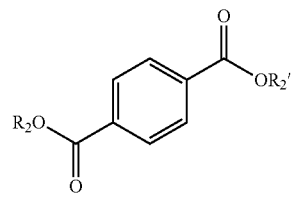

In Chemical Formula 2, $R_2$ and $R_2'$ may each independently be the same or different, and may be hydrogen, or a straight or branched chain alkyl group having 1 to 20 carbon atoms, preferably 4 to 20 carbon atoms, more preferably 5 to 20 carbon atoms, and even more preferably 5 to 10 carbon atoms.

Specific examples of the terephthalate compound include dibutyl terephthalate (DBTP), dioctyl terephthalate (DOTP), diisononyl terephthalate (DINTP), diisodecyl terephthalate (DIDTP), etc., but are not limited thereto. These compounds can be used alone or in combination of two or more.

The isophthalate compound may be represented by Chemical Formula 3 below.

[Chemical Formula 3]

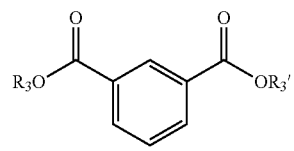

In Chemical Formula 3, $R_3$ and $R_3'$ may each independently be the same or different, and may be hydrogen, or a straight or branched chain alkyl group having 1 to 20 carbon atoms, preferably 4 to 20 carbon atoms, more preferably 5 to 20 carbon atoms, and even more preferably 5 to 10 carbon atoms.

Specific examples of the isophthalate compound include dibutyl isophthalate (DBIP), dioctyl isophthalate (DOIP), diisononyl isophthalate (DINIP), diisodecyl isophthalate (DIDIP), etc., but are not limited thereto. These compounds can be used alone or in combination of two or more.

Preferably, as the phthalate compound, dioctyl terephthalate (DOTP) may be used.

The purity of the phthalate compound may be about 98% or higher, preferably about 99.5% or higher, and more preferably about 99.9% or higher, but is not limited thereto. Phthalate compounds of any quality and purity which are commercially available can be used.

The phthalate compound may be obtained by an esterification reaction of an acid, such as phthalic acid, terephthalic acid, and isophthalic acid, or an anhydride thereof, with an alcohol. In order to neutralize catalysts used in the esterification reaction and the remaining acid components after the esterification reaction, basic compounds such as sodium carbonate ($Na_2CO_3$), sodium hydroxide (NaOH), calcium carbonate ($CaCO_3$), and potassium hydroxide (KOH) are used. Accordingly, impurities such as metal ions, such as $Na^+$, $K^+$, and $Ca^{2+}$ liberated from such basic compounds, metal salt compounds produced by binding with the metal ions, or other reaction by-products may remain in a trace amount in the phthalate compounds.

When a trace amount of these metal ions or metal salt compounds is contained in the phthalate compounds, there is no significant influence on the quality of the phthalate compounds themselves, but they can act as a catalyst poison to the hydrogenation catalyst used in the hydrogenation reaction of the phthalate compounds, thereby becoming one of the main causes for lowering the activity of the catalyst. More specifically, the metal ions or metal salt compounds exist in a state of not being sufficiently dissolved or dispersed and can be readily physically or chemically adsorbed by the hydrogenation catalyst, and thus the activity of the catalyst is drastically lowered.

However, according to the hydrogenation method of the present invention, the alcohols having two or more carbon atoms used in the hydrogenation reaction effectively dissolve the metal ions, the metal salt compounds, or other impurity components to prevent the adsorption to the hydrogenation catalyst, thereby playing a role in maintaining the activity of the hydrogenation catalyst. Examples of the alcohols having two or more carbon atoms may be at least one selected from ethanol, n-propanol, isopropanol, n-butanol, isobutanol, pentanol, hexanol, heptanol, octanol (n-octanol, 2-ethylhexanol), nonanol, decanol, undecanol, and dodecanol, which are aliphatic alcohols having 2 to 12 carbon atoms, and preferably 2 to 10 carbon atoms, or a mixture thereof.

Further, the hydrogenation catalyst includes at least one selected from the group consisting of ruthenium (Ru), palladium (Pd), rhodium (Rh), platinum (Pt), and nickel (Ni).

Hereinafter, the present invention will be described in more detail by way of examples. However, these examples are given for illustrative purposes only, and the scope of the invention is not intended to be limited by these examples.

EXAMPLES

Example 1

20 parts by weight of octanol was mixed with 100 parts by weight of dioctyl terephthalate (DOTP) having purity of 99%, and then the mixture was injected into a catalytic reactor through a pump. The mixture of DOTP and octanol was preheated at a pressure of 150 bar and a temperature of 120° C., while hydrogen ($H_2$) was also preheated at the same pressure and temperature, and then each was supplied to the upper portion of the reactor. Herein, the catalyst used in the reactor was a ruthenium (Ru) catalyst having a cylindrical shape with a diameter of 3.2 mm and a height of 3 mm.

The hydrogenation reaction was initiated, followed by continuous reaction at an initial reaction conversion rate of 66%, and when the reaction conversion rate dropped to 33.6%, the reaction was terminated.

Then, after confirming that the activity of the catalyst had deteriorated, octanol was supplied to the catalytic reactor at a temperature of 150° C. to perform the catalyst regeneration operation for 1 hour.

Subsequently, the conversion rate at the rear end portion of the reactor was measured after reintroducing the reactant, and as a result, it was confirmed that the conversion rate was recovered to 75.4% relative to the initial conversion rate in which the new catalyst was used.

Example 2

The hydrogenation reaction and catalyst regeneration operation were performed in the same manner as in Example 1, except that the temperature during the catalyst regeneration using octanol was 180° C.

Subsequently, the conversion rate at the rear end portion of the reactor was measured after reintroducing the reactant, and as a result, it was confirmed that the conversion rate was recovered to 82.4% relative to the initial conversion rate in which the new catalyst was used.

Example 3

The hydrogenation reaction and catalyst regeneration operation were performed in the same manner as in Example 1, except that the catalyst regeneration time using octanol was 5 hours.

Subsequently, the conversion rate at the rear end portion of the reactor was measured after reintroducing the reactant, and as a result, it was confirmed that the conversion rate was recovered to 82.1% relative to the initial conversion rate, in which the new catalyst was used.

Example 4

The hydrogenation reaction and catalyst regeneration operation were performed in the same manner as in Example 1, except that the catalyst regeneration time using octanol was 5 hours and the catalyst regeneration temperature was 180° C.

Subsequently, the conversion rate at the rear end portion of the reactor was measured after reintroducing the reactant, and as a result, it was confirmed that the conversion rate was recovered to 91.3% relative to the initial conversion rate, in which the new catalyst was used.

Comparative Example 1

The hydrogenation reaction and catalyst regeneration operation were performed in the same manner as in Example 1, except that the catalyst regeneration time using octanol was 5 hours and the catalyst regeneration temperature was 50° C.

Subsequently, the conversion rate at the rear end portion of the reactor was measured after reintroducing the reactant, and as a result, it was confirmed that the conversion rate was recovered to 15.5% relative to the initial conversion rate, in which the new catalyst was used.

Comparative Example 2

The hydrogenation reaction and catalyst regeneration operation were performed in the same manner as in Example 1, except that the catalyst regeneration time using methanol was 5 hours.

Subsequently, the conversion rate at the rear end portion of the reactor was measured after reintroducing the reactant, and as a result, it was confirmed that the catalyst performance rather deteriorated to 28.5%, which was lower than the conversion rate of 33.6% before the regeneration.

Although specific parts of the present invention has been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A method for regenerating a hydrogenation catalyst for a phthalate compound, comprising the steps of
    performing a hydrogenation reaction of a phthalate compound including reacting a phthalate compound with hydrogen in the presence of a hydrogenation catalyst in a catalyst reactor, and then
    regenerating the hydrogenation catalyst at a temperature of 80° C. or more by supplying an alcohol to the catalyst reactor,
    wherein the hydrogenation catalyst includes at least one selected from the group consisting of ruthenium (Ru), palladium (Pd), rhodium (Rh), platinum (Pt), and nickel (Ni).

2. The method for regenerating a hydrogenation catalyst for a phthalate compound of claim 1, wherein the alcohol is at least one selected from the group consisting of octanol, hexanol, butanol, propanol, ethanol, 2-ethylhexanol, and an alcohol having an isomer structure of the alcohols.

3. The method for regenerating a hydrogenation catalyst for a phthalate compound of claim 1, wherein the step of regenerating the hydrogenation catalyst is performed at a temperature of 80 to 300° C. by supplying an alcohol to the catalyst reactor such that the Reynolds number of the alcohol passing through a catalyst layer is 2100 or more.

4. The method for regenerating a hydrogenation catalyst for a phthalate compound of claim 1, further comprising a step of continuously reusing the regenerated catalyst in the hydrogenation reaction of a phthalate compound after the step of regenerating the hydrogenation catalyst.

5. The method for regenerating a hydrogenation catalyst for a phthalate compound of claim 1, wherein the phthalate compound is at least one selected from the group consisting of phthalate, terephthalate, isophthalate, and a carboxylic acid compound thereof.

6. The method for regenerating a hydrogenation catalyst for a phthalate compound of claim 1, wherein the phthalate compound includes a metal ion or a metal salt compound as an impurity.

7. The method for regenerating a hydrogenation catalyst for a phthalate compound of claim 1, wherein the purity of the phthalate compound is 98% or higher.

8. The method for regenerating a hydrogenation catalyst for a phthalate compound of claim 1, wherein the phthalate compound is dioctyl terephthalate (DOTP).

9. The method for regenerating a hydrogenation catalyst for a phthalate compound of claim 1, wherein the hydrogenation reaction of the phthalate compound is performed by additionally using an alcohol having 2 or more carbon atoms.

* * * * *